(12) United States Patent
Drechsler

(10) Patent No.: US 11,386,551 B2
(45) Date of Patent: Jul. 12, 2022

(54) METHOD AND APPARATUS FOR BUFFY COAT IMAGING

(71) Applicant: PERKINELMER HEALTH SCIENCES, INC., Waltham, MA (US)

(72) Inventor: Thomas R. Drechsler, Waltham, MA (US)

(73) Assignee: PERKINELMER HEALTH SCIENCES, INC., Waltham, MA (US)

( * ) Notice: Subject to any disclaimer, the term of this patent is extended or adjusted under 35 U.S.C. 154(b) by 3 days.

(21) Appl. No.: 16/184,494

(22) Filed: Nov. 8, 2018

(65) Prior Publication Data
US 2020/0151870 A1 May 14, 2020

(51) Int. Cl.
| | |
|---|---|
| G06K 9/00 | (2022.01) |
| G06T 7/00 | (2017.01) |
| G06T 7/70 | (2017.01) |
| B01D 21/26 | (2006.01) |
| G01N 21/27 | (2006.01) |
| G01N 33/49 | (2006.01) |
| H04N 5/225 | (2006.01) |
| H04N 9/07 | (2006.01) |

(52) U.S. Cl.
CPC .......... *G06T 7/0012* (2013.01); *B01D 21/262* (2013.01); *G01N 21/27* (2013.01); *G01N 33/491* (2013.01); *G06T 7/70* (2017.01); *G06T 2207/10141* (2013.01); *G06T 2207/30004* (2013.01); *H04N 5/2256* (2013.01); *H04N 9/07* (2013.01)

(58) Field of Classification Search
None
See application file for complete search history.

(56) References Cited

U.S. PATENT DOCUMENTS

| | | | | |
|---|---|---|---|---|
| 4,939,925 | A | * 7/1990 | Sakuma | G01N 33/491 73/61.63 |
| 5,763,265 | A | 6/1998 | Itsuzaki et al. | |
| 7,450,224 | B2 | 11/2008 | Maroney et al. | |
| 2005/0026765 | A1* | 2/2005 | Escal | B04B 5/0421 494/20 |

(Continued)

FOREIGN PATENT DOCUMENTS

| | | |
|---|---|---|
| WO | 2006037941 A1 | 4/2006 |
| WO | 2011019576 A1 | 2/2011 |
| WO | 2017132169 A1 | 8/2017 |

OTHER PUBLICATIONS

McQuillan et al., "Designing an automated blood fractionation system", International Journal of Epidemiology 2008; 37: i51-i55.

(Continued)

*Primary Examiner* — Sean M Conner
(74) *Attorney, Agent, or Firm* — Day Pitney LLP; Valeriya Svystun; Anthony A. Kassas

(57) ABSTRACT

A blood sample processor for imaging a centrifuged blood sample is provided including a transparent container with the centrifuged blood sample therein. An illumination source is positioned to illuminate the centrifuged blood sample at a non-right angle to the transparent container. A digital camera disposed opposite the transparent container images the centrifuged blood sample and the image is processed to determine the relative locations of component layers of the centrifuged blood sample.

16 Claims, 3 Drawing Sheets

(56) References Cited

U.S. PATENT DOCUMENTS

| | | | | |
|---|---|---|---|---|
| 2008/0045394 A1* | 2/2008 | Kolenbrander | ............ | G06T 7/12 |
| | | | | 494/7 |
| 2008/0111988 A1* | 5/2008 | Maroney | ................ | G01N 15/05 |
| | | | | 356/39 |
| 2010/0317106 A1* | 12/2010 | Levine | ................. | G01N 33/491 |
| | | | | 435/372 |
| 2011/0226045 A1 | 9/2011 | McQuillan | | |
| 2012/0140230 A1* | 6/2012 | Miller | ................. | G01N 15/042 |
| | | | | 356/441 |
| 2013/0201482 A1* | 8/2013 | Munro | ................ | A61M 5/1689 |
| | | | | 356/407 |
| 2015/0362352 A1* | 12/2015 | Garrepy | ................ | G01N 21/78 |
| | | | | 73/37 |
| 2018/0372715 A1* | 12/2018 | Kluckner | ............. | G01N 21/314 |

OTHER PUBLICATIONS

International Search Report and Written Opinion of the International Searching Authority, issued in corresponding International application No. PCT/US2019/057535, dated Jan. 23, 2020. (13 pp).

* cited by examiner

METHOD AND APPARATUS FOR BUFFY COAT IMAGING

BACKGROUND OF THE INVENTION

1. Field of the Invention

The present invention relates to a method and apparatus for determining the location of component layers in a blood sample after centrifugation. More particularly, the present invention relates to a method and apparatus for creating high-contrast images of a centrifuged blood sample to establish locations of component layers therein.

2. Description of the Related Art

Blood samples are often analyzed or processed by centrifuging the blood sample to separate out particular components of the blood sample into component layers. Typically, the centrifuged blood sample comprises three component layers, the top plasma layer, the bottom red blood cell layer and the middle "buffy coat" layer containing white blood cells. Centrifugation allows particular components of interest to be extracted from the blood sample by removal of the appropriate component layer.

The component layers of the blood sample are typically extracted manually in turn by a pipette. The component layer containing the component of interest is retained for analysis and the other component layers may be retained or disposed of as desired. Manual extraction of the blood sample component layers in this manner is time consuming and expensive. It also requires considerable skill as, to the naked eye, the boundaries between blood sample component layers can be difficult to distinguish. These problems are exacerbated if the buffy coat layer is the fraction of interest, as the buffy coat layer is typically relatively thin compared to the other blood sample component layers.

Proper illumination of the blood sample and the component layers within is critical to providing a high-contrast image which may be reliably analyzed. Commonly, reflections interfere with the image and require complex hardware or software filtering.

It is therefore an object of the present invention to provide a method and apparatus for the automated illumination and imaging of a centrifuged blood sample.

SUMMARY OF THE INVENTION

In accordance with an embodiment of the invention, a blood sample processor for imaging a centrifuged blood sample is provided including a transparent container with the centrifuged blood sample therein. An illumination source is positioned to illuminate the centrifuged blood sample at an oblique angle to the transparent container. A digital camera disposed opposite the transparent container images the centrifuged blood sample and the image is processed to determine the relative locations of component layers of the centrifuged blood sample.

In accordance with a further embodiment of the invention, a pipette with a liquid level height sensor is provided for determining the actual location of the top of the centrifuged blood sample and for removing component layers therefrom.

In accordance with a further embodiment of the invention, a processor is provided to determine the actual locations of component layers of the centrifuged blood sample.

Accordingly, accurate detection of the location of the buffy coat layer allows automated collection of any of the discrete component layers of a centrifuged blood sample. Detection of the buffy coat layer may be done by optical imaging, using a camera to image the container with the centrifuged blood sample therein and algorithms to post-process the centrifuged blood sample image to quantitatively analyze the vertical location of each component layer within the container.

BRIEF DESCRIPTION OF THE DRAWINGS

The features and advantages of the invention are apparent from the following description taken in conjunction with the accompanying drawings in which.

DETAILED DESCRIPTION OF THE INVENTION

After centrifugation, there can be distinguished a layer of clear fluid (the plasma), a layer of red fluid containing most of the red blood cells, and a thin layer in between. The buffy coat layer is the fraction of an anticoagulated blood sample that contains most of the white blood cells and platelets following density gradient centrifugation of the blood.

Figure 1:
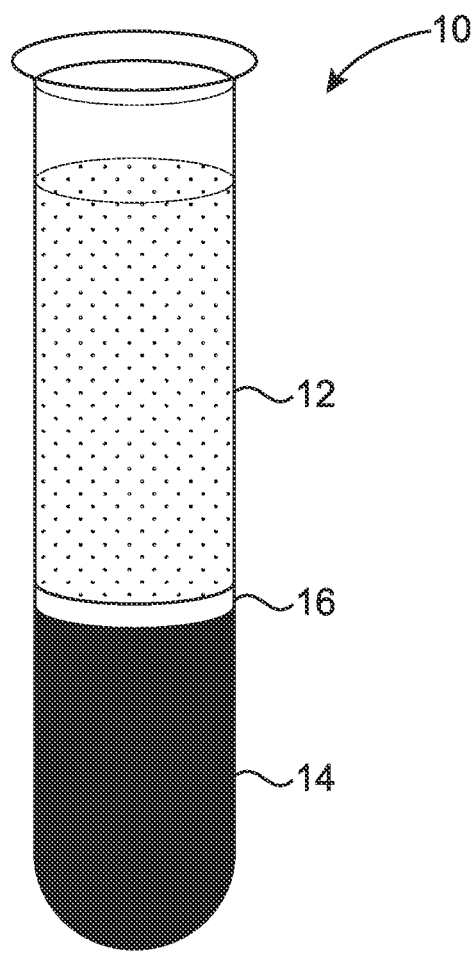
FIG. 1 is an illustration of a test tube with a centrifuged blood sample therein.

Referring to FIG. 1, a blood sample after centrifugation is shown in test tube 10. The blood sample has three component layers; a plasma layer 12 at the top of the test tube, a red blood cell layer 14 at the bottom of the test tube and an intermediate or buffy coat layer 16. In some instances, a clean buffy coat layer is approximately 1 mm thick. Above the clean buffy coat layer is a transition buffy coat layer that is approximately 3-4 mm thick. Together the clean buffy coat layer and the transition buffy coat layer make up the buffy coat layer.

Typically, only the clean buffy coat layer is desired for processing. Accordingly, first the plasma layer 12 is removed. Then, the transition layer of the buffy coat layer 16 is eliminated. The clean buffy coat layer is then topmost in test tube 10 and available for removal.

To properly remove each of the layers, the layers must be adequately illuminated and distinguished. This may be accomplished by illuminating test tube 10 with a light source and then obtaining an image of the test tube and its contents. An illumination source or a light source is used to illuminate the contents of the test tube 10. In some instances, the light source can be a monochromatic light source, while in other instances the light source can comprise multiple monochromatic light sources that are spectrally mixed. Examples of monochromatic light sources include LEDs that emit light having a wavelength of less than 570 nm. These light sources can be colored light that is produced by one or more LEDs. In further embodiments, the light source or multiple light sources can be filtered or un-filtered light.

Figure 2:
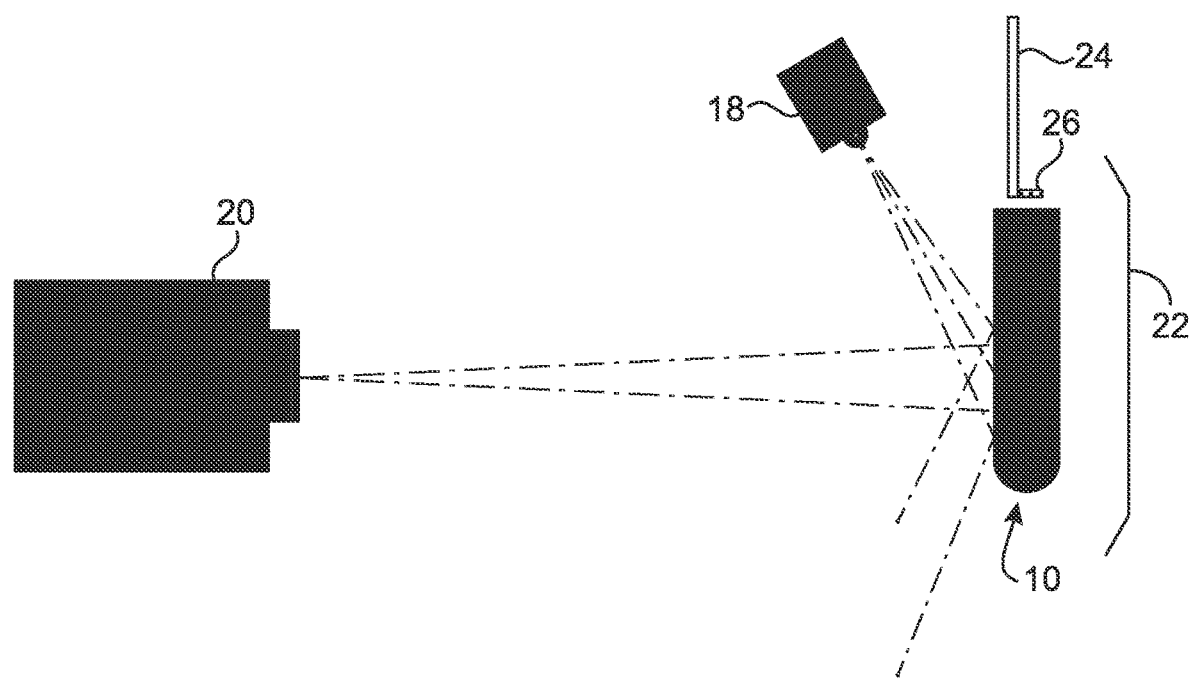
FIG. 2 is an illustration of a blood sample processor in accordance with the invention.

FIG. 2 shows a blood sample processor providing an illumination source 18 in accordance with an embodiment of the invention. Tuning to obtain optimum contrast between sample layers in test tube 10 is accomplished by choosing the proper wavelengths of light for illumination source 18. When illuminated, the plasma layer of a sample typically reflects or casts a yellow or amber tinted light having a wavelength of approximately 570 nm or greater, while the red blood layer reflects a red light having a wavelength of approximately 680 nm or greater. Therefore in order to minimize reflection and backscatter from the plasma and red blood layers of the sample, and further isolate the buffy coat layer, it is advantageous to illuminate the sample with a light source having a wavelength less than 570 nm. In some instances this light source can be a blue light with a wavelength of 470 nm, in others it can be a green light, while in still others an ultra-violet light source can be used. In each instance, however, the light source has a wavelength less than 570 nm, which maximizes reflection from the buffy coat layer and more specifically from the clean buffy coat layer.

In some instances, the illumination or light source 18 can have a LED or other light emitting element that emits light having a wavelength less than 570 nm. In other instances, the light source 18 can have multiple light emitting elements that emit light having different wavelengths. These multi-chromatic light sources can, in many instances, maximize reflection of light by the buffy coat layer by enhancing the differentiation between the buffy coat layer and the plasma and red blood cell layers, thereby increasing the resolution of the image of the buffy coat layer. For example, multiple LEDs having different wavelengths can be used to achieve light having different hues or color temperatures. Mixing light source wavelengths can also enhance the differentiation between the transition buffy coat layer and the clean buffy coat layer. In particular, certain light wavelengths increase the amount of reflection by the transition buffy coat layer, but not the clean buffy coat layer; while other light wavelengths increase the amount of reflection by the clean buffy coat layer but not the transition buffy coat layer. Mixing this group of two or more disparate light sources with two or more different wavelengths can increase reflection of both the transition buffy coat layer and the clean buffy coat layer. These disparate light sources can be different colored light sources having different color temperatures or hues.

Illumination source 18 is preferably high intensity LEDs, for example, Luxeon Rebel Color LEDS and, more particularly, the multi-LED blue (470 nm) 3 LED boards. In other instances, other LEDs, LED packages, or light sources can be used. LEDs can be individual LEDs incorporated onto a single circuit board or can be multiple LED chips integrated into a single chip. While LEDs are preferably used, other methods could include an illumination source other than a LED, where the non-LED source is passed through one or more spectral filters to isolate light having a wavelength less than 570 nm.

Illumination source 18 can be positioned approximately 30 degrees off of the center axis of test tube 10. It may be appreciated that any number of offset angles (i.e., an oblique angle to the test tube) would be appropriate for the illumination source so long as the angle is sufficient to prevent reflection and other interference. For example, in some instances the illumination source 18 can be positioned at any angle between 15 and 30 degrees off of the center axis of test tube 10. In still other examples, the illumination source 18 can be positioned at any angle between 45 and 30 degrees off of the center axis of test tube 10.

A digital camera 20 is positioned opposite test tube 10 for imaging of the test tube 10 and the blood sample within. Preferably, a color camera, rather than a black and white camera, is used because a color camera may accentuate buffy coat layer 16. In some instances, a suitable camera for this purpose may be the Cognex Advantage 100Series, Part No. ADV102C from Cognex Corporation (Natick, Mass.). In other instances, any high resolution camera can be used. It will be appreciated that digital camera 20 must be calibrated prior to imaging. It may also be appreciated that illumination source 18 may be triggered by digital camera 20.

Advantageously, almost all test tubes with blood samples for imaging will have a label. Accordingly, imaging of the blood sample may be done through the clear side of test tube 10 and the test tube label may be used as a reflector. Exposure time for digital camera 20 may be optimized based on saturation level of the camera. It may be appreciated that the exposure for digital camera 20 should be set below the saturation point to insure a quality image.

A light shield 22 may be also be provided for use in imaging test tube 10 with the blood sample within. The use of a light shield with, for example, a black background may reduce ambient light thereby improving imaging of the blood sample.

In order to determine the position of the component layers, test tube 10 with the centrifuged blood sample therein is positioned vertically opposite digital camera 20. An image of the test tube 10 and the blood sample within is then captured by digital camera 20. The image may then be processed by a suitable processor 100 using photo processing algorithms using pixel count to determine the relative locations of the component layers within test tube 10. A suitable hardware/software system for this application may be a 2-D vision system available from Cognex Corporation (Natick, Mass.).

Light shield 22 may include an external reference against which test tube 10 and the blood sample within may be imaged. This will provide for direct location of the layers from the image. The external reference may also be incorporated into the blood sample processor or the rack that the test tube is in.

Processor 100 of the blood sample processor may also control an automatic pipette 24. The automatic pipette has a liquid level height sensor 26 for detecting the fluid surface of the blood sample. Once the actual location of the fluid surface of the blood sample is known, the relative locations may be used to set the actual locations of each component layer of the blood sample. As the dimensions of test tube 10 are known, the pipette 24 may be inserted into the blood sample to a desired location and a volume of liquid aspirated equal to the calculated volume of a particular layer. Typically, the layers are aspirated in turn starting with the top or plasma layer.

As an example, if it is desired to extract the buffy coat layer for analysis, the pipette may be used to aspirate the plasma layer 12 to a level just above the upper boundary of buffy coat layer 16. The pipette 24 may then be used to aspirate the buffy coat layer 16 to a level just below the lower boundary of the buffy coat layer 16. The buffy coat layer 16 of the blood sample in the pipette 24 may then be transferred to another container for analysis.

In a case where a sample of the clean buffy coat layer is required for analysis, the plasma layer 12 may be aspirated, and then the transition layer of buffy coat layer 16 may be aspirated. Finally, the clean buffy coat layer may be aspirated and transferred to another container for analysis.

It may be appreciated that aspiration locations for the buffy coat layer will depend on a particular application. Assays that use downstream secondary processing can afford to collect above and below the buffy coat layer to obtain the entirety of the layer. Biobank harvesting applications may "guardband" the buffy coat layer by going past the top plasma layer and stopping short of the bottom red blood cell layer to ensure minimal contamination.

Figure 3:
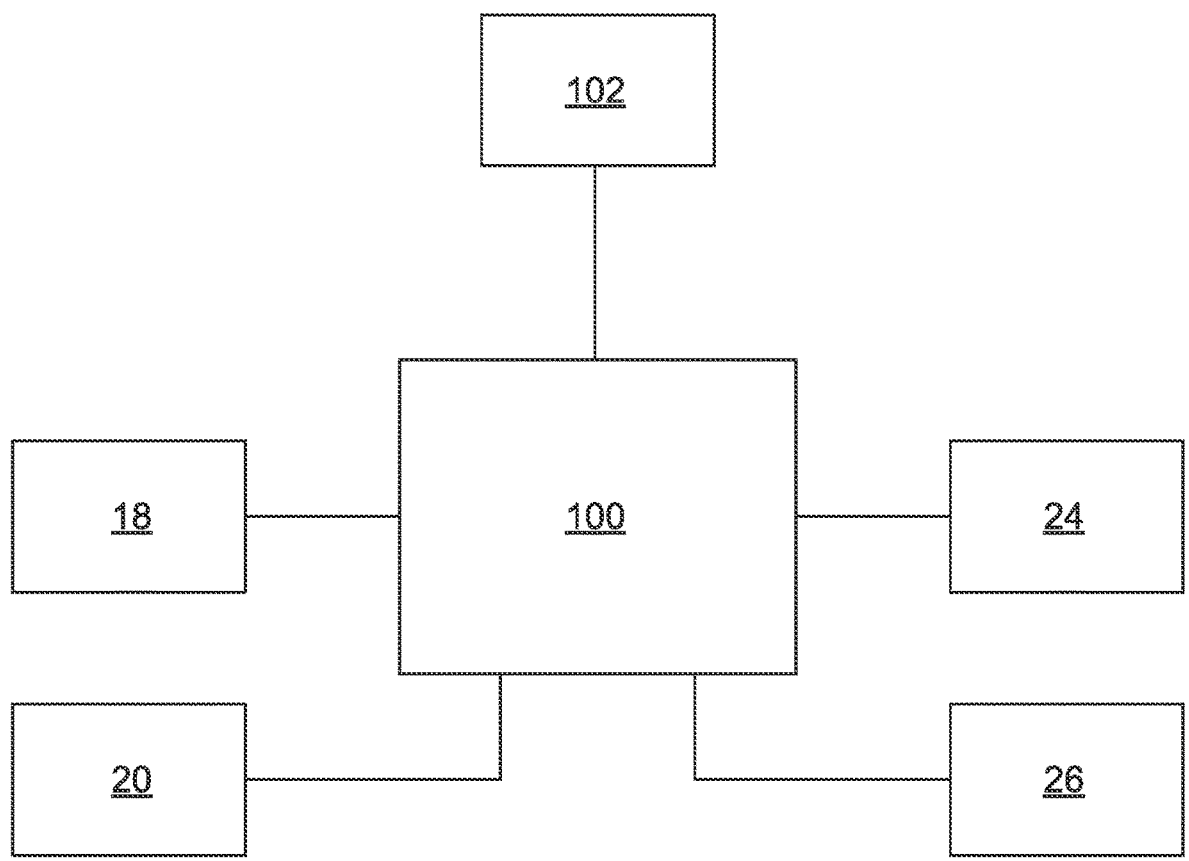
FIG. 3 is a schematic block diagram of the logical interconnections of the blood sample processor.

FIG. 3 shows how the various components of the blood sample processor may be logically connected. The sample processor 100 is connected directly to illumination source 18, digital camera 20, pipette 24 and liquid height level sensor 26. The processor 100 may also be provided with a user interface 102. The processor 100 may also control the illumination of test tube 10 with the blood sample during imaging. In so doing, illumination source 18 may be either strobed or constant on. In a preferred embodiment, the sample processor 100 and the user interface 102 may be provided by a computer system. In some instances, the illumination source 18, camera 20, pipette 24, liquid height level sensor 26 and processor 100 may be included in a single system or machine that can be used to analyze blood samples. This single system can further include a user interface 102 that can be used to control the single machine. In some cases, the steps of the method can be automated by a program executed by the processor 100 of the machine.

It is of course to be understood that the invention is not to be limited to the details of the above embodiment, which is described by way of example only. Many variations are possible within the scope of the following claims.

The invention claimed is:

1. A blood sample processor for imaging a centrifuged blood sample, comprising:
    a transparent container with the centrifuged blood sample therein;
    an illumination source for illuminating the centrifuged blood sample, positioned at an oblique angle off of a center axis of the transparent container;
    a digital camera disposed opposite the transparent container for imaging the centrifuged blood sample; and
    a processor for processing the centrifuged blood sample image and determining relative locations of component layers of the centrifuged blood sample,
    wherein the processor comprises a liquid level height sensor for detecting a location of a surface of the centrifuged blood sample by mechanical contact of the liquid level height sensor with the surface; and
    wherein the processor determines actual locations of the component layers of the centrifuged blood sample based on the relative locations of component layers of the centrifuged blood sample and the location of the surface of the centrifuged blood sample.

2. The blood sample processor of claim 1, wherein the illumination source uses monochromatic light below a yellow wavelength.

3. The blood sample processor of claim 1, wherein the illumination source uses multiple wavelengths of light below a yellow wavelength.

4. The blood sample processor of claim 3, wherein the multiple wavelengths of light are selected to highlight each of a clean buffy coat layer and a transition layer.

5. The blood sample processor of claim 1, wherein the illumination source illuminates the centrifuged blood sample at a 30 degree angle to the transparent container.

6. The blood sample processor of claim 1, wherein the digital camera is a color digital camera.

7. The blood sample processor of claim 1, further comprising an external reference for determining actual locations of the component layers of the centrifuged blood sample.

8. The blood sample processor of claim 1, further comprising a pipette for removal of the component layers of the centrifuged blood sample from the transparent container.

9. A method of analyzing a centrifuged blood sample, comprising:
    placing the blood sample in a transparent container;
    illuminating the centrifuged blood sample with an illumination source positioned at an oblique angle off of a center axis of the transparent container;
    imaging the centrifuged blood sample with a digital camera disposed opposite the transparent container;
    processing the centrifuged blood sample image and determining relative locations of component layers of the centrifuged blood sample;
    detecting a location of a surface of the centrifuged blood sample by mechanical contact of a liquid level height sensor with the surface of the centrifuged blood sample; and
    determining actual locations of the component layers of the centrifuged blood sample based on the relative locations of component layers of the centrifuged blood sample and the location of the surface of the centrifuged blood sample.

10. The method of analyzing a centrifuged blood sample of claim 9, further comprising illuminating the centrifuged blood sample using monochromatic light below a yellow wavelength.

11. The method of analyzing a centrifuged blood sample of claim 9, further comprising illuminating the blood sample using multiple wavelengths of light below a yellow wavelength.

12. The method of analyzing a centrifuged blood sample of claim 11, further comprising selecting the multiple wavelengths of light to highlight each of a clean buffy coat layer and a transition layer.

13. The method of analyzing a centrifuged blood sample of claim 9, further comprising illuminating the centrifuged blood sample at a 30 degree angle to the transparent container.

14. The method of analyzing a centrifuged blood sample of claim 9, further comprising using a color digital camera for the digital camera.

15. The method of analyzing a centrifuged blood sample of claim 9, further comprising using an external reference for determining actual locations of the component layers of the centrifuged blood sample.

16. The method of analyzing a centrifuged blood sample of claim 9, further comprising using a pipette to remove the component layers of the centrifuged blood sample from the transparent container.

* * * * *